United States Patent [19]
Watanuki et al.

[11] Patent Number: 5,171,872
[45] Date of Patent: Dec. 15, 1992

[54] METHOD FOR THE PREPARATION OF AN OXIMESILANE WITHOUT COLORATION

[75] Inventors: Isao Watanuki, Myougi; Hiroshi Tsumura, Annaka; Kazushi Satoh, Tokyo; Nobuhiko Kodana, Tomioka, all of Japan

[73] Assignee: Shin-Etsu Chemical Company, Limited, Tokyo, Japan

[21] Appl. No.: 779,192

[22] Filed: Oct. 22, 1991

[30] Foreign Application Priority Data

Oct. 22, 1990 [JP] Japan .................................. 2-283861

[51] Int. Cl.$^5$ ................................................ C07F 7/10
[52] U.S. Cl. .................................................... 556/422
[58] Field of Search .......................................... 556/422

[56] References Cited

U.S. PATENT DOCUMENTS

| | | | |
|---|---|---|---|
| 4,033,991 | 7/1977 | Shinohara et al. | 556/422 X |
| 4,126,630 | 11/1978 | Müller et al. | 556/422 |
| 4,380,660 | 4/1983 | Mathew et al. | 556/422 |
| 4,384,131 | 5/1983 | Kanner | 556/422 |
| 4,400,527 | 8/1983 | Mathew et al. | 556/422 |
| 4,918,209 | 4/1990 | Baule | 556/422 |
| 4,925,964 | 5/1990 | Zoche | 556/422 |
| 4,990,642 | 2/1991 | Häring | 556/422 X |

FOREIGN PATENT DOCUMENTS 2611719  9/1988  France .................................. 556/422

*Primary Examiner*—Paul F. Shaver
*Attorney, Agent, or Firm*—Millen, Whitem, Zelano and Branigan

[57] ABSTRACT

An improvement is proposed for minimizing coloration of an oximesilane synthesized by the reaction of a chlorosilane such as vinyl trichlorosilane and an oxime compound such as methyl ethyl ketone oxime in the presence of a nitrogen-containing basic compound as an acceptor of the hydrogen chloride followed by the removal of the precipitates of the hydrogen chloride salt of the base and distillation. The improvement comprises conducting the distillation of the filtrate after removal of the precipitates of salt is performed in the presence of a nitrogen-containing basic compound such as ammonia in the filtrate, for example, by blowing ammonia gas into the liquid under distillation. An already colored oximesilane product also can be decolorized by blowing ammonia gas thereinto.

8 Claims, No Drawings

METHOD FOR THE PREPARATION OF AN OXIMESILANE WITHOUT COLORATION

BACKGROUND OF THE INVENTION

The present invention relates to a method for the preparation of an oximesilane such as methyl tris(methylethylketoxime) silane, vinyl tris(methylethylketoxime) silane and the like with little coloration.

One of the prior art methods for the synthetic preparation of an oximesilane is a method in which a chlorosilane such as methyl trichlorosilane and the like and an oxime compound such as methyl ketoxime and the like in an amount stoichiometrically equivalent to the chlorosilane are reacted in the presence of a stoichiometrically equivalent amount of an acceptor of the hydrogen chloride produced as a by-product of the reaction (see, for example, Japanese Patent Publication 39-29837). The acid acceptor can be an organic basic compound such as pyridine. In this method, however, it is an indispensable step that the reaction product is separated and isolated from the hydrochloride of the organic base, for example, by filtration and distillation. A serious problem in this distillation process is the danger of explosion so that this method is disadvantageous as an industrial process for the production of an oximesilane.

An alternative method is disclosed in Japanese Patent Publication 1-21834 according to which a chlorosilane compound is reacted with an oxime compound in an amount twice as large as the stoichiometrically equivalent amount. In this method, the excess of the oxime compound over stoichiometry serves as an acceptor of hydrogen chloride.

Further alternatively, Japanese Patent Kokai 63-227592 teaches a continuous method for the preparation of an oximesilane compound in which the hydrogen chloride acceptor is ammonia gas blown into the stoichiometric mixture of a chlorosilane compound and an oxime compound. The amount of the ammonia is larger by 1.04 to 1.46 times than the stoichiometric amount.

A problem common in all of these prior art methods is that the oximesilane product produced by the method is readily colored in yellow or brown when a trace amount or, for example, a few ppm of a heavy metal salt such as iron (III) chloride and the like is present in the reaction mixture. The drawback can of course be solved if the starting materials could be purified to an extremely high purity and the apparatuses used in the reaction could be so designed as not to cause contamination of the reaction mixture with heavy metals although it would be almost hopeless in an industrial process to fully achieve these ideal conditions due to the great technological difficulties and the prohibitingly large costs.

It is known that the above mentioned phenomenon of coloration of the oximesilane compound is very remarkable when the temperature is 90° C. or higher. It is also known that the coloration reaction of an oximesilane compound is greatly accelerated by the presence of unreacted chlorine in the reaction mixture so that the coloration of the oximesilane into brown rapidly proceeds even at a temperature as low as 60° C. or lower. When unreacted chlorine is contained in the reaction mixture, coloration of the oximesilane product proceeds particularly in the step of isolation and purification of the oximesilane from the reaction mixture which usually is performed at an elevated temperature.

In the preparation method of oximesilanes using ammonia as the acceptor of hydrogen chloride, in particular, the reaction hardly reaches completion as compared with the other preparation methods leaving a considerable amount of the unreacted chlorine so that this problem of coloration is very serious. The reason therefor is presumably that the reaction proceeds by involving the gaseous, liquid and solid phases caused as an influence of the ammonium chloride produced as a by-product.

In view of the difficulties above described in obtaining an uncolored product of an oximesilane, it is eagerly desired to develop a method for obtaining an uncolored or little colored oximesilane product by preventing coloration of the reaction mixture, in particular, in the steps of isolation and purification of the oximesilane from the reaction mixture after completion of the reaction.

SUMMARY OF THE INVENTION

The present invention accordingly has an object to provide an improved method for the preparation of an oximesilane by the reaction of a halogenosilane with an oxime compound by which the oximesilane product obtained can be prevented from coloration.

Thus, the present invention provides an improvement, in the method for the preparation of an oximesilane represented by the general formula $$(R^2R^3C=N-O-)_a SiR^1_{4-a}, \quad (I)$$

in which $R^1$ is a hydrogen atom or a unsubstituted or halogen-substituted alkyl, alkenyl, aryl, aralkyl or cycloalkyl group, $R^2$ and $R^3$ are each, independently from the other, a hydrogen atom or an unsubstituted or halogen-substituted alkyl, alkenyl, aryl, cycloalkyl, cycloalkenyl or aralkyl group and the subscript a is a positive integer not exceeding 4, by the reaction of a halogenosilane represented by the general formula $$R^1_{4-a}SiX_a, \quad (II)$$

in which $R^1$ and the subscript a each have the same meaning as defined above and X is a halogen atom, and an oxime compound represented by the general formula $$R^2R^3C=N-OH, \quad (III)$$

in which $R^2$ and $R^3$ each have the same meaning as defined above, in the presence of a nitrogen-containing basic compound and an organic solvent followed by the removal of the hydrogen halide salt of the nitrogen-containing basic compound produced by the reaction from the reaction mixture and isolation of the oximesilane from the reaction mixture, which comprises conducting the treatment for the isolation of the oximesilane from the reaction mixture in the presence of a nitrogen-containing basic compound in the reaction mixture.

DETAILED DESCRIPTION OF THE PREFERRED EMBODIMENTS

As is described above, the most characteristic feature of the invention according to the invention consists in the step of isolation of the oximesilane from the reaction mixture after completion of the reaction between a halogenosilane and an oxime compound. Namely, the treatment for the isolation of the oximesilane from the reaction mixture is conducted in the presence of a nitrogen-containing basic compound, which can be the same one as or different one from that used as the acid acceptor in the reaction, in the reaction mixture.

The nitrogen-containing basic compound is exemplified by ammonia and amine compounds including alkyl and aryl amines such as methylamine, ethylamine, butylamine, aniline, pyridine and the like. In particular, the improvement obtained by the present invention is remarkable when the nitrogen-containing basic compound is ammonia.

The organic solvent used in the reaction of the halogenosilane and oxime compound according to the invention should preferably have a relatively low boiling point as exemplified by n-hexane, petroleum ether, toluene and the like. The organic solvent has an effect to decrease the viscosity of the reaction mixture so that the reactivity between the reactants can be enhanced and the separation of the hydrogen halide of the basic compound from the oximesilane product can be facilitated.

One of the reactant pertaining to the reaction according to the invention is a halogenosilane represented by the above given general formula (II). Examples of the halogenosilane compounds to which the present invention is applicable include tetrachlorosilane, trimethyl chlorosilane, dimethyl dichlorosilane, methyl trichlorosilane, methyl ethyl dichlorosilane, ethyl trichlorosilane, diethyl dichlorosilane, triethyl chlorosilane, n-propyl trichlorosilane, isopropyl trichlorosilane, 2-chloroethyl trichlorosilane, 3-chloropropyl trichlorosilane, vinyl trichlorosilane, vinyl methyl dichlorosilane, propenyl trichlorosinale, allyl trichlorosilane, phenyl trichlorosilane, benzyl trichlorosilane and the like. In particular, the improvement obtained by the invention is remarkable when the halogenosilane is methyl, ethyl or vinyl trichlorosilane.

The other reactant pertaining to the reaction with the above described halogenosilane is an oxime compound represented by the above given general formula (III). The group denoted by $R^2$ or $R^3$ excepting hydrogen atom is exemplified by methyl, ethyl, propyl, butyl, pentyl, hexyl, vinyl, butenyl, cyclopentyl, cyclohexyl, cyclooctyl, 3-methyl-1-cyclohexyl, cyclopentenyl, cyclohexenyl, phenyl, tolyl, xylyl and benzyl groups.

Particular examples of the oxime compound which can be the reactant in the reaction according to the invention comprises: acetoaldehyde oxime, acetone oxime, 2-hexanone oxime, 1-butyraldehyde oxime, 4-penten-2-one oxime, methyl ethyl ketone oxime, benzaldehyde oxime, acetophenone oxime, benzophenone oxime, benzyl ethyl ketone oxime, cinnamaldehyde oxime, cyclohexyl methyl ketone oxime, cyclopentanone oxime, cyclohexanone oxime, 2-methylcyclopentanone oxime, 2-methylcyclohexanone oxime, 2-chlorocyclohexanone oxime, 2-ethylcyclopentanone oxime and the like.

The reaction of the above described halogenosilane and oxime compound can be performed according to a conventional procedure although it is desirable that the conditions of the reaction are selected so as to decrease coloration of the resultant oximesilane product as far as possible. The hydrogen halide produced by the reaction reacts with the nitrogen-containing basic compound to form a salt which precipitates in the reaction mixture.

After completion of the reaction, the reaction mixture is filtered to remove the precipitated hydrogen halide salt of the nitrogen-containing basic compound and the filtrate of the reaction mixture is subjected to the treatment for the isolation of the oximesilane compound, for example, by distillation. The essential feature of the improvement according to the invention consists in that the reaction mixture under the treatment contains a nitrogen-containing basic compound so that coloration of the oximesilane product obtained by the treatment can be greatly decreased. Even when the reaction mixture has already been colored to some extent, an oximesilane product with little coloration can be obtained by conducting the treatment in the presence of a nitrogen-containing basic compound in the reaction mixture.

The nitrogen-containing basic compound to be contained in the reaction mixture under the treatment can be the same one as used as the hydrogen halide acceptor in the reaction of the halogenosilane and oxime compound. The amount of this nitrogen-containing basic compound in the reaction mixture is in the range, usually, from 0.001 to 0.1 mole per mole of the oximesilane compound contained in the reaction mixture. No particular additional advantages can be obtained by increasing the amount of the nitrogen-containing basic compound to exceed the above mentioned upper limit. When the nitrogen-containing basic compound is ammonia, it is usually sufficient to continuously blow ammonia gas into the reaction mixture under treatment such as distillation. This amount of the basic compound can be contained in the reaction mixture already at the start of the treatment or, if necessary, can be introduced into the reaction mixture subsequently in the course of the treatment.

The reaction mixture under the isolation treatment of the oximesilane product should be kept at a temperature, preferably, 90° C. or below or, more preferably, 80° C. or below. Provided that the requirement for this temperature condition is satisfied, the isolation treatment of the oximesilane can be performed safely with minimum coloration even by the method of distillation under industrial conditions during which intense coloration of the product may readily take place otherwise.

In this way, the present invention gives a great advantage that a high-quality oximesilane products can easily be obtained with minimum coloration. For example, the oximesilanes prepared from methyl ethyl ketone oxime and methyl trichlorosilane or vinyl trichlorosilane according to the invention can be used quite satisfactorily as a functionality-imparting agent or a cross-linking agent in the preparation of room temperature-curable silicone rubber compositions.

In the following, the present invention is described in more detail by way of examples and a comparative example although the scope of the invention is never limited thereby.

EXAMPLE 1

Into a flask of 3 liter capacity equipped with a reflux condenser, stirrer, thermometer, dropping funnel and a gas inlet tube reaching the bottom of the flask were introduced 454 g of methyl ethyl ketone oxime and 702 g of anhydrous toluene. While keeping the mixture in the flask at a temperature of 55° to 65° C. under agitation, 270 g of vinyl trichlorosilane containing 15 ppm by weight of iron (III) chloride were added thereto dropwise through the dropping funnel at a rate of 2.3 g per minute along with continuous introduction of ammonia gas from the gas inlet tube at a rate of 180 ml per minute. After completion of the dropwise addition of the silane compound, the reaction mixture was further agitated for 1 hour under continued introduction of ammonia gas to complete the reaction followed by filtration to remove the precipitates of ammonium chloride. The filtrate was subjected to distillation at 80° C. under a reduced pressure of 5 to 15 mmHg to remove toluene as the solvent and the unreacted methyl ethyl ketone oxime taking 2 hours, during which ammonia gas was continuously blown into the filtrate in the flask at a rate of 50 ml per minute.

The residual liquid in the flask was analyzed by the gas cromatography to find that the liquid contained 94.6% by weight of vinyl tris(methyl ethyl ketoxime) silane. The color of this liquid was APHA 50 according to the standard specified in JIS K 1557.

COMPARATIVE EXAMPLE

The experimental procedure was substantially the same as in Example 1 described above except that distillation of the filtrate after removal of the precipitates of ammonium chloride to remove toluene and unreacted starting oxime compound was conducted without blowing of ammonia gas into the filtrate.

The residual liquid after distillation was analyzed by the gas chromatography to find that the content of the vinyl tris(methyl ethyl ketoxime) silane therein was 93.6%. The coloration of the liquid was at least 500 in the APHA scale and 12 in the Gardner color scale according to JIS K 6901.

EXAMPLE 2

Ammonia gas was blown at a rate of 500 ml per minute into the oximesilane product prepared in Comparative Example described above at room temperature for 1 hour to find that coloration of the silane was decreased to APHA 400.

What is claimed is:

1. In a method for the preparation of an oximesilane represented by the general formula $$(R^2R^3C=N-O-)_a SiR^1_{4-a},$$

in which $R^1$ is a hydrogen atom or an unsubstituted or halogen-substituted alkyl, alkenyl, aralkyl or cycloalkyl group, $R^2$ and $R^3$ are each, independently from the other, a hydrogen atom or an unsubstituted or halogen-substituted alkyl, alkenyl, aryl, cycloalkyl, cycloalkenyl or aralkyl group and the subscript a is a positive integer not exceeding 4, by the reaction of a halogenosilane represented by the general formula $$R^1_{4-a}SiX_a,$$

in which $R^1$ and the subscript a each have the same meaning as defined above and X is a halogen atom, and an oxime compound represented by the general formula $$R^2R^3C=N-OH,$$

in which $R^2$ and $R^3$ each have the same meaning as defined above, in the presence of a nitrogen-containing basic compound and an organic solvent followed by the removal of the hydrogen halide salt of the nitrogen-containing basic compound produced by the reaction from the reaction mixture and isolation of the oximesilane from the reaction mixture, an improvement which comprises conducting the treatment for the isolation of the oximesilane from the reaction mixture in the presence of a nitrogen-containing basic compound in the reaction mixture, wherein the nitrogen-containing basic compound is added to the reaction mixture after completion of the reaction and prior to or during the isolation treatment.

2. The improvement as claimed in claim 1 in which the nitrogen-containing basic compound contained in the reaction mixture under the treatment for the isolation of the oximesilane from the reaction mixture is ammonia.

3. The improvement as claimed in claim 1 in which the amount of the nitrogen-containing basic compound contained in the reaction mixture under the treatment for the isolation of the oximesilane from the reaction mixture is in the range from 0.001 to 0.1 mole per mole of the oximesilane.

4. The improvement as claimed in claim 1 in which the treatment for the isolation of the oximesilane from the reaction mixture is conducted by distillation of the reaction mixture.

5. The improvement of claim 1, wherein the reaction mixture to be subjected to isolation treatment contains the solvent, product, and excess oxime.

6. The improvement of claim 1, wherein the nitrogen-containing basic compound present during the isolation treatment is ammonia, methylamine, ethylamine, butylamine, aniline, and pyridine.

7. In a method for the preparation of an oximesilane represented by the general formula $$(R^2R^3C=N-O-)_a SiR^1_{4-a},$$

in which $R^1$ is a hydrogen atom or an unsubstituted or halogen-substituted alkyl, alkenyl, aralkyl or cycloalkyl group, $R^2$ and $R^3$ are each, independently from the other, a hydrogen atom or an unsubstituted or halogen-substituted alkyl, alkenyl, aryl, cycloalkyl, cycloalkenyl or aralkyl group and the subscript a is a positive integer not exceeding 4, by the reaction of a halogenosilane represented by the general formula $$R^1_{4-a}SiX_a,$$

in which $R^1$ and the subscript a each have the same meaning as defined above and X is a halogen atom, and an oxime compound represented by the general formula $$R^2R^3C=N-OH,$$

in which $R^2$ and $R^3$ each have the same meaning as defined above, in the presence of a nitrogen-containing basic compound and an organic solvent followed by the removal of the hydrogen halide salt of the nitrogen-containing basic compound produced by the reaction from the reaction mixture and isolation of the oximesilane from the reaction mixture, the improvement which comprises conducting the treatment for the isolation of the oximesilane from the reaction mixture in the presence of a nitrogen-containing basic compound in the reaction mixture, and wherein the treatment for isolation of the oximesilane from the reaction mixture is conducted by distillation of the reaction mixture under blowing of ammonia gas into the reaction mixture.

8. A method for the decolorization of a colored oximesilane product which comprises blowing ammonia gas into the colored oximesilane product.

* * * * *